Figure 1:
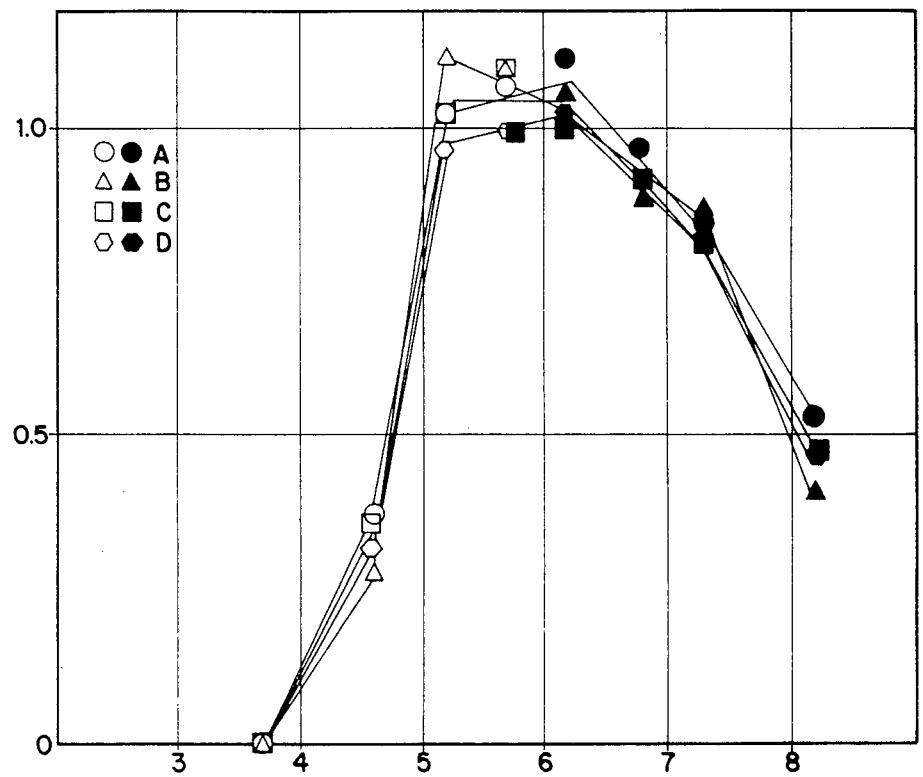

| United States Patent [19] | [11] Patent Number: 4,642,288 |
|---|---|
| Elia De Miguel et al. | [45] Date of Patent: Feb. 10, 1987 |

[54] PROCESS FOR PRODUCING THERMOSTABLE ALPHA-AMYLASES BY CULTURING MICRO-ORGANISMS AT ELEVATED TEMPERATURES

[75] Inventors: María-Fe Elia De Miguel, La Moraleja; Pedro Miró Roig; Eulalia Pares Olivet, both of Madrid, all of Spain

[73] Assignee: Compania Espanola de Petroleos, S.A., Spain

[21] Appl. No.: 630,958

[22] Filed: Jul. 16, 1984

[30] Foreign Application Priority Data

Oct. 11, 1983 [ES] Spain ............................. 526.406

[51] Int. Cl.$^4$ .................. C12P 19/14; C12N 9/28; C12R 1/07
[52] U.S. Cl. ........................... 435/99; 435/202; 435/832
[58] Field of Search ............................ 435/99, 202

[56] References Cited

U.S. PATENT DOCUMENTS

| 3,849,194 | 11/1974 | Armbruster et al. | 435/202 X |
| 4,284,722 | 8/1981 | Tamuri et al. | 435/202 X |
| 4,447,532 | 5/1984 | Coker et al. | 435/99 |
| 4,473,645 | 9/1984 | Horwath | 435/202 |
| 4,540,663 | 9/1985 | Witt | 435/99 |

FOREIGN PATENT DOCUMENTS 1296839  11/1972  United Kingdom ................ 435/202

*Primary Examiner*—Lionel M. Shapiro
*Attorney, Agent, or Firm*—McGlew and Tuttle

[57] ABSTRACT

A process to obtain a new thermostable and neutral α-amylase by cultivating a strain selected from microorganisms Bacillus sp. NCIB 11887 or NCIB 11886, or any of the mutants thereof, at temperatures from 50° to 70° C.

8 Claims, 2 Drawing Figures

PROCESS FOR PRODUCING THERMOSTABLE ALPHA-AMYLASES BY CULTURING MICRO-ORGANISMS AT ELEVATED TEMPERATURES

OBJECT OF THE INVENTION

The present invention refers to a process for obtaining an α-amylase enzyme by the submerged culturing of thermophilic micro-organisms at temperatures of from 50° to 70° C., said α-amylase enzyme being obtained in a state highly resistant to elevated temperatures even in the presence of low calcium concentrations and under the conditions normally employed in processes for the enzymatic hydrolysis of starch. The preferred micro-organisms are selected from the group consisting of the species *Bacillus circulans, Bacillus licheniformis,* Bacillus sp.

TECHNICO-ECONOMIC JUSTIFICATION

The applications of enzymes in processes for hydrolyzing starch have been known for many years, in substitution of the acid catalysed processes which, since they require more severe operating conditions, produce rather negative degradation of the carbohydrates, particularly when the products should be employed for food purposes.

These enzymatic processes generally comprise two steps: on the one hand, by enzymes classified as α-amylases, more or less random fragments are produced in the long chain polysaccharides constituting the starch, with a substantial decrease in the viscosity of the starch slurry, known as the liquefaction step. In the second step, the thusly obtained solution having a low viscosity is treated with enzymes of the amyloglucosidase type which liberate the glucose monosaccharide molecules, which step is consequently known as saccharification.

This invention refers to α-amylase enzymes, the applications whereof can be very varied, both in processes for hydrolyzing corn, potato or barley starch, as well as in detergent compositions to promote the action thereof on the stains.

The enzyme, for each of these applications, should have certain particular characteristics, wherefore it is rather difficult to propose one enzyme having characteristics which are suitable for all its possible applications.

The first commercially used microbial α-amylases originated from strains of *Bacillus subtilis* and the use thereof has been known for many years. However, for the majority of the applications of these enzymes a special emphasis is placed on the stability thereof under elevated temperature conditions or under adverse conditions. In turn, the effect of the calcium ion as the stabilizing factor of the enzymatic activity is widely described. Hence, the calcium ion concentration is, in many uses, severely limited by the conditions of the process (for example, presence of calcium sequestering agents in detergent formulations) or the addition thereof produces an economical problem since it should be removed again, after the liquefaction step, due to its adverse effect in the following steps or in the quality of the end product.

Therefore, it can be stated that at present the requirement of a high thermal stability under low calcium ion conditions constitutes the common denominator of the properties of a commercial α-amylase. Some stabilizing factors of the enzymes of *B. subtilis* to improve the thermal stability thereof under typical conditions of hydrolyzing the starch have been described, for example, in U.S. Pat. No. 3,272,717 of J. Fukumoto of Japan, or U.S. Pat. No. 3,524,798 in the name of Standard Brands Inc. Hydrolyzing processes operating at temperatures below that of gelatination, in the range of from 60° to 75° C., have also been claimed, for example, in U.S. Pat. No. 3,922,196 and U.S. Pat. No. 3,922,200 of C.P.C. However, the most widely accepted processes include a prior gelatination step at 105°–110° C. for about 5 minutes, which requires the presence of α-amylases which are intrinsically more stable than those of *Bacillus subtilis*. Strains producing remarkably more stable enzymes have been described in the latest years. Thus, for example, British Pat. No. 1,296,839 of 1972 granted to Novo departed from the *Bacillus licheniformis*, U.S. Pat. No. 3,697,378 of 1972 granted to Glaxo Laboratories departed from *Bacillus coagulans*, and also U.S. Pat. No. 4,284,722 of 1981 granted to CPC International Inc. departed from *Bacillus stearothermophilus*, and introducing the culture of a specific micro-organism under thermophilic conditions. However, it should be noted that some enzymes (specifically useful in detergents) are claimed as rather stable at elevated pH, for example in U.S. Pat. No. 4,061,541 and U.S. Pat. No. 4,022,666, and others (specially suitable for the hydrolysis of corn starch) are claimed as rather stable under neutral conditions or even under acid conditions (U.S. Pat. No. 4,284,722).

Although there is not an absolute homogenity within each category, there is a remarkable difference between the conventional group of non-thermostable enzymes and the new group of thermostable enzymes. One of the known products of this latter group is commercialized under the registered name of Termamyl of NOVO and originates from a *Bacillus licheniformis*.

The group of conventional non-thermostable enzymes is characterized in that its maximum activity is reached between 50° and 65° C., while in the thermostable enzymes said maximum activity occurs in the range of from 75° to 85° C. Thus, the value of the quotient of the activity at 80° C., when compared with the activity at 50° C., will be a good indicator of the thermostability of an enzyme, especially if recorded in the absence of calcium ion.

In the search for new thermostable enzymes, it is reasonable to expect a higher probability of success if research is directed to the group of thermophilic micro-organisms, i.e. adapted to grow at temperatures of from 50° to 75° C., since the protein and enzymatic systems thereof should be better adapted to elevated growing temperatures. In fact, said suspicion is confirmed by reviewing Table I.

TABLE I

| Strain | Ratio $\frac{\text{activity } 80° \text{ C.}}{\text{activity } 50° \text{ C.}}$ (without Ca++) |
|---|---|
| (a) Mesophilic micro-organisms | |
| B. Subtilis (ATCC 6051A) | 0.75 |
| B. subtilis (ATCC 21770) | 0.28 |
| B. cereus (ATCC 21769) | 0.66 |
| B. amyloliquefaciens (ATCC 23842) | 0.02 |
| B. subtilis (NRRL B 3411) | 0.17 |
| B. licheniformis (NCIB 8059) | 0.50 |
| B. licheniformis (NCIB 8061) | 1.00 |
| B. licheniformis (ATCC 6598) | 1.42 |
| B. licheniformis (ATCC 6634) | 1.14 |
| B. licheniformis (ATCC 8480) | 1.32 |

TABLE I-continued

| Strain | Ratio $\frac{\text{activity } 80°\text{ C.}}{\text{activity } 50°\text{ C.}}$ (without $Ca^{++}$) |
|---|---|
| B. licheniformis (ATCC 11945) | 1.50 |
| (b) Thermophilic micro-organisms | |
| B. stearothermophilus (ATCC 15951) | 1.8 |
| B. stearothermophilus (ATCC 31195) | 1.95 |
| B. stearothermophilus (ATCC 31196) | 2.10 |
| B. stearothermophilus (ATCC 31197) | 2.18 |
| B. stearothermophilus (ATCC 31198) | 1.60 |
| B. stearothermophilus (ATCC 31199) | 1.48 |
| Lactobacillus acidophilus (ATCC 31283) | 1.7 |
| B. circulans (ATCC 21822) | 1.7 |

On the other hand, the exception of the mesophiles comprised of Bacillus licheniformis, studied and claimed, for example, in British Pat. No. 1,296,839 of NOVO, to a range of cultivation temperatures of from 25° to 50° C. as maximum limits, is remarkable, therefore raising the question as to whether said particular heat stability is only and exceptionally attributable to the α-amylase produced, or whether the other cellular systems are also specially protected against the high temperatures. In this case, the micro-organism could readily be adapted to be cultured under thermophilic conditions. A first indication in this direction originates from U.S. Pat. No. 4,348,480 of 1982 assigned to Miles Laboratories, which described culturing of a B. licheniformis in xylose-enriched media at a temperature of from 50° to 60° C. for the production of glucose isomerase. It has been discovered that said capacity is not an exception particular of said strain, but other strains of said species, such as Bacillus licheniformis NCIB 11874 and Bacillus licheniformis ATCC 27811, can be cultivated in simple media to produce α-amylase, once certain precautions have been taken concerning the adaptation thereof to temperatures in the range of 60° C.

The practical advantages of culturing at high temperatures mainly originate from a saving in the design of the fermentors since the cooling system necessary to remove the fermentation heat at 30°-35° C. is almost overcome when operating at 55°-60° C., and from a lesser ease in contamination of the culture and a better maintenance of the sterility conditions at temperatures above 55° C. It is not recommendable to increase the temperatures above 60°-65° C. although some micro-organisms present growths at temperatures in the range of 70° C. since the solubility of the oxygen in the culture medium decreases with the temperature, and if same is too high large flows of air and elevated agitations may be required to avoid low oxygen concentrations in the cellular medium which would, in general, cause these micro-organisms to direct their metabolisms through an anaerobia via with a slight production of acids, wherefore these working conditions would not be too recommendable for the production of the enzyme.

Besides, the biological processes are accelerated at high temperatures requiring lower cultivation times than with lower temperatures to reach a given enzymatic activity in the broth. As will be seen from the examples, this reduction in the fermentation time can become very important, permitting large increases in the productivity of the fermentors. Therefore, there is also included within the scope of this invention, the specific process for culturing certain strains of B. licheniformis at temperatures above 50° C. for the production of α-amylase.

TECHNICAL DESCRIPTION

Thermostable α-amylase producing micro-organisms have been selected from different thermophilic bacteria deposited in Micro-organism Collections, for example, NCIB (National Collection of Industrial Bacteria, Torry Research Station, P.O. Box 31, 135 Abbey Road, Aberdeen AB9 8DE, Scotland), NRRL (Northern Utilization Research and Development Division, Department of Agriculture, Peroia, Ill., U.S.A.) and ATCC (American Type Culture Collection, 12301 Parklawn Drive, Rockville, Md. 20852, U.S.A.). As mentioned in the Technico-Economical Justification, a higher possibility of finding thermostable α-amylases was expected in micro-organisms whose growth took place at temperatures above or at 50° C. than in those whose optimum growth took place at 25°-37° C.

To facilitate the search for thermostable α-amylase producing micro-organisms, a plate activity test was carried out. The test was based on the halo formed about an α-amylase producing colony when an iodine solution was poured onto a Petri plate on which a micro-organism has grown from a culture medium containing starch. Specifically, the strain to be tested was reseeded in an AM-8 culture medium (see Example 1) and it was incubated for about 48 hours at an optimum growing temperature. Thereafter, 10 ml of a suspension containing 1% (weight/volume) of starch and 1% (weight/volume) of agar were poured onto the plate. The agar was then allowed to solidify and the plates were immediately incubated for 15 minutes at 80° C. Thereafter, the plates were cooled and developed using a solution of lugol. Finally, after 5 minutes' reaction, the sizes of the halos formed about each colony was determined. In general, there was an acceptable correlation between the diameter of the halo and the α-amylase activity of the colony in question.

In our search for thermostable α-amylase producing micro-organisms, we tested 32 thermophilic micro-organisms corresponding to the following species: B. circulans, B. coagulans, B. licheniformis, B. stearothermophilus, L. acidophilus, Thermus sp., Microbispora thermodiastatica, Micropolyspora faeni, Micropolyspora sp., Thermus thermophilus, Thermoactinomyces vulgaris, Microbispora bispora, Bacillus sp.

This semi-quantitative and rapid test permitted us to select 9 α-amylase producing micro-organisms whose enzymatic activity was determined according to the following protocol:

A 4% (weight/volume) solution of starch in a 0.02M phosphate buffer, pH 5.7, having a 0.006M NaCl concentration, was heated to about 50° C. Likewise the culture broth whose activity had to be determined (conveniently diluted in the same buffer as the starch) was heated to the same temperature. Then 0.5 ml of the mentioned enzymatic suspension and 0.5 ml of the starch solution, both previously preheated, were poured into a test tube. The mixture was incubated for 5 minutes at 50° C. under magnetic stirring. The reaction was stopped by sharply dropping the temperature and adding 1 ml of Bernfeld reagent. Said reagent was prepared as follows: a solution containing 16 gr of NaOH/200 ml of $H_2O$ (in any case distilled $H_2O$ is used throughout this specification) was poured on 300 ml of H₂O close to boiling point, then 10 g of 3,5-dinitrosalicylic acid and 300 g of Rochelle salt (potassium sodium tartrate) were added, the mixture was heated until the reagents were completely dissolved and finally it was leveled to 1 liter. The samples were then heated in a bath containing boiling water for 5 minutes. After the mentioned period of time, the samples were cooled and 10 ml of H₂O were added. Finally, the absorbance of each sample was determined at 540 nm compared with a blank prepared with H₂O and the Bernfeld reagent.

A cepsa α-amylase unit is defined as the milligrams of reducing sugars, measured as maltose, produced per minute under the previously mentioned testing conditions. Thus:

$$\text{Cepsa } \alpha\text{-amylase units/ml of broth} = \frac{\text{mg of maltose produced/ml} \ldots \times D \times d}{t}$$

where,
D: dilution effected in the culture broth
d: dilution effected in the reaction medium
t: reaction time (min.)

Therefore, the absorbance units at 540 nm of each sample should be converted into milligrams of reducing sugars measured as maltose. Thus, maltose samples were prepared having concentrations of from 0.5 to 5.0 mg/ml and the true content in reducing sugars thereof was determined by the Bernfeld reagent. Thus, a standard sample was obtained which joined absorbance at 540 nm with the reducing sugar content, measured as maltose. From said standard there was determined, by interpolation, the real content in reducing sugars of each sample, once the $A_{540}$ corresponding to the sugars present in the starch or in the culture broth had been deducted, to the measurement for each case. That is to say, that:

$$(A_{540})_{true} = (A_{540})_{measured} - (A_{540})_{starch} - (A_{540})_{broth}.$$

It should be taken into account that the α-amylase activity has been determined in all the cases according to this test and, therefore, all the enzymatic units mentioned in the text corredpond to cepsa α-amylase units. The only exception corresponds to the activities measured at 80° C. (see Table 1). In said case, the protocol differs only in the temperature used in the reaction of the mentioned enzymatic suspension with the starch, since it is of 80° C. instead of 50° C. Using this quantitative test to determine the α-amylase activity and based on the ratio of activities at 80° and 50° C. (Table 1), four micro-organisms capable of producing high amounts of thermostable enzymes were selected, in this first approach.

Table 2 illustrates the activities of these bacteria, as well as the culturing conditions thereof.

TABLE 2

| Micro-organism | Culturing Conditions | | |
|---|---|---|---|
| | Medium | Temp. (°C.) | Agitation (r.p.m.) |
| B. licheniformis ATCC 27811 | AM-76 | 56 | 210 |
| B. Licheniformis NCIB 11874 | AM-79 | 56 | 210 |
| Bacillus sp. NCIB 11887 | AM-79 | 56 | 210 |
| B. Circulans ATCC 21822 | AM-79 | 56 | 210 |

TABLE 2-continued

| Micro-organism | Culturing Conditions | | |
|---|---|---|---|
| | Medium | Temp. (°C.) | Agitation (r.p.m.) |
| ATCC 21822 | | | |

Results obtained under said conditions:

| Micro-organism | Time (hr) | α-Amylase activity Cepsa α-amylase μ/ml broth |
|---|---|---|
| B. Licheniformis ATCC 27811 | 96 | 172 |
| B. Licheniformis NCIB 11874 | 48 | 161 |
| Bacillus sp. NCIB 11887 | 24 | 263 |
| B. Circulans ATCC 21822 | 24 | 100 |

All these cultures were conducted in 250 ml Erlenmeyer flasks containing 100 ml of medium
See Examples 1 and 4 for the composition of the culture media The strains of this invention, and mainly Bacillus sp. NCIB 11887, have been subjected to the action of different mutagenic agents with the purpose of increasing the α-amylase producitivity thereof. Spontaneous mutations during culture are known, but unfortunately the low frequency thereof prevents the direct selection of superproducing colonies of a particular enzyme. Fortunately, the proportion of mutants can be increased in a colony by using mutagens which induce changes in the bacterial genotype. These mutagenic agents can have a chemical or a physical nature. Among the chemical agents mainly used by us is N-methyl-N'-nitro-nitrous guanidine (NG). The NG is characterized by its capacity to produce high mutation frequencies even for high survival indexes. The use of NG takes place during the exponential growth of the culture in question, since its maximum effectiveness occurs during the replication of the gens. On the other hand, the ultra-violet type radiations have been the main physical agent used. Its action mechanism in the induction of mutuations in the mentioned micro-organism differs from that attributed to NG. This fact enhances the use in series of both mutagens, thereby obtaining a synergic effect in the increase of the α-amylase productivity.

In our case, the use of the precisely mentioned mutagens permits a series of characteristics of the strains of the present invention to be improved. Said characteristics are mainly two: production level of α-amylase and partial or total unrepression of the synthesis of the enzyme. However, it should be taken into account that the mutants obtained produce amylases whose characteristics coincide with those of the enzyme synthesized by its progenitor, especially, from the point of view of the thermostability thereof.

The synthesis of these α-amylases is clearly influenced by the components of the culture medium. As the majority of hydrolytic enzymes, the production thereof takes place in the final phases of the culture since the synthesis thereof is repressed. In general, an appropriate culture medium should contain a source of assimilable carbon, a source of nitrogen and other necessary nutrients.

It has been observed that there are numerous utilizable sources of carbon: starch, starch hydrolysate, malt extract, maltose, lactose, glycerol, lactic, etc. The concentration used of these carbon sources ranges of from 0.1 to 5% (weight/volume) and preferably of from 1 to 3%. The most suitable sources of carbon are soluble starch, obtained by the partial acid hydrolysis of potato starch. The most appropriate amounts of soluble starch range of from 20 to 40 g/l of culture medium. Said amounts correspond to cultures in the fermentor, where the pH is controlled by preventing it from being adjusted to below 5.0. When the culture takes place in erlenmeyer flasks, the pH is not controlled, wherefore it has a tendency to be acidified and, consequently, the synthesis of α-amylase is inhibited. To avoid these problems two measures are adopted: buffered media are always used and the concentration of the starch in the culture medium is reduced to 0.1–1.5% and, preferably to 0.5–1.0%. Under these conditions, the formation of acids is minimized and although the level of synthesized enzyme is lowered with respect to the fermentors with a higher starch concentration and a controlled pH, it permits the different cultures to be compared readily and economically.

The appropriate nitrogen sources in the culture medium can be inorganic or organic. The former includes ammonium salts and inorganic nitrates. Suitable organic nitrogen sources include yeast extract, peptone, hydrolysate of casein, soybean meal, meat extract, corn steep liquor, lactic serum, milk, triptone, cotton seeds, etc. Preferably, the yeast extract or the peptone, in a concentration of from 1.1 to 2% and, preferably, from 0.3 to 0.8%. Besides, the culture media should contain various inorganic salts, such as sodium chloride, magnesium sulphate, calcium chloride, calcium carbonate, etc. Likewise, cellular growth and enzymatic productivity can be increased by adding vitamins, aminoacids, etc., at a trace level. These sources of carbon and nitrogen, as well as the remaining nutrients, can be used either alone or in combination, as can be seen from the composition of the culture media cited in the Examples.

The cultivation conditions used for the production of these α-amylases coincide with those generally used to culture other thermophilic bacteria. The cultures are, preferably, submerged, under aeration and agitation, at 50°–70° C., pH 5–9, for 1 to 5 days.

As previously mentioned, the synthesis of α-amylase takes place when cellular growth has terminated. From this moment, the enzyme is accumulated in the culture broth. Once the enzyme has been produced, fermentation is stopped and the broth is cooled to 4° C. The cells and other solid residues are then eliminated by filtration or centrifugation of the broth, recovering the α-amylase in a liquid phase. This filtrate having α-amylase activity is denominated crude α-amylase in subsequent references (Example 7). Said crude enzyme can be purified by conventional methods, such as the addition of organic salts or solvents. In the first case, ammonium sulphate, sodium sulphate, magnesium sulphate, potassium sulphate, sodium citrate, sodium chloride, potassium chloride, etc. can be used. In the event organic solvents are used, the α-amylases can be precipitated and recovered by adding methanol, ethanol, acetone, isopropanol, 1,4-dioxane, etc. Likewise, the α-amylase can be recovered from the culture broth by absorption in starch or by liquid-liquid extraction in mixtures of polyethylene glycol-dextrane. We prefer the addition of organic solvents to concentrate and purify the crude enzyme. A suitable control of the temperature during precipitation prevents the α-amylase from being denaturalized. The most suitable solvent is acetone, the addition of which (60% volume/volume) to the crude enzyme permits precipitation of the α-amylase. The precipitate is recovered by filtration or centrifugation and it is re-suspended in a 0.05M Tris-HCl buffer, ph 7.0.

The average yield of the purifications is above 80% and the purification reached ranges from 1.5 to 2 times with respect to the specific activity of the crude enzyme. The final suspension of the α-amylase in a buffer shall be denominated "partially purified α-amylase" in subsequent references (Example 7).

The α-amylases of this invention were distinguished with respect to the influence of distinct physical factors on the activity thereof. The main physical factors which affect the activity and optimum stability, are the pH and temperature, although other parameters can also affect the reactions. The effects observed in the process, as a result of the variations in the pH and/or temperature, are due both to the direct influence thereof on the reaction (ionization, dissociation, solubility, variation in the reaction rate, displacement of the equilibrium, etc.), as well as to the action thereof on the enzyme itself ($K_m$, $V_{max}$ and stability).

FIG. 1 illustrates the effect of the pH. The abscissa reflects the pH/room temperature units and the ordinate reflects the relative activity of the enzyme, according to the standard test at 80° C., with respect to the activity measured at pH=5.8, in the presence of about 10–20 ppm calcium ion and in a 0.1M acetate buffer, for pH's below 5.7 and a 0.2M phosphate buffer for pH's above 5.7. Curve A corresponds to the enzyme of *B. Stearothermophilus* ATCC 31199, curve B to *B. licheniformis* NCIB 11874 and curve C to Bacillus sp. NCIB 11887 and curve D to *B. Circulans* ATCC 21822. As can be seen the α-amylases of this invention, just as that produced by *B. Stearothermophilus* ATCC 31199 described in U.S. Pat. No. 4,284,722, seem to be especially suitable for the liquefaction of the starch, since they present activity at slightly acid pH values, thereby restricting the maltulose formation and facilitate the coupling with the subsequent enzymatic saccharification step.

Figure 2:
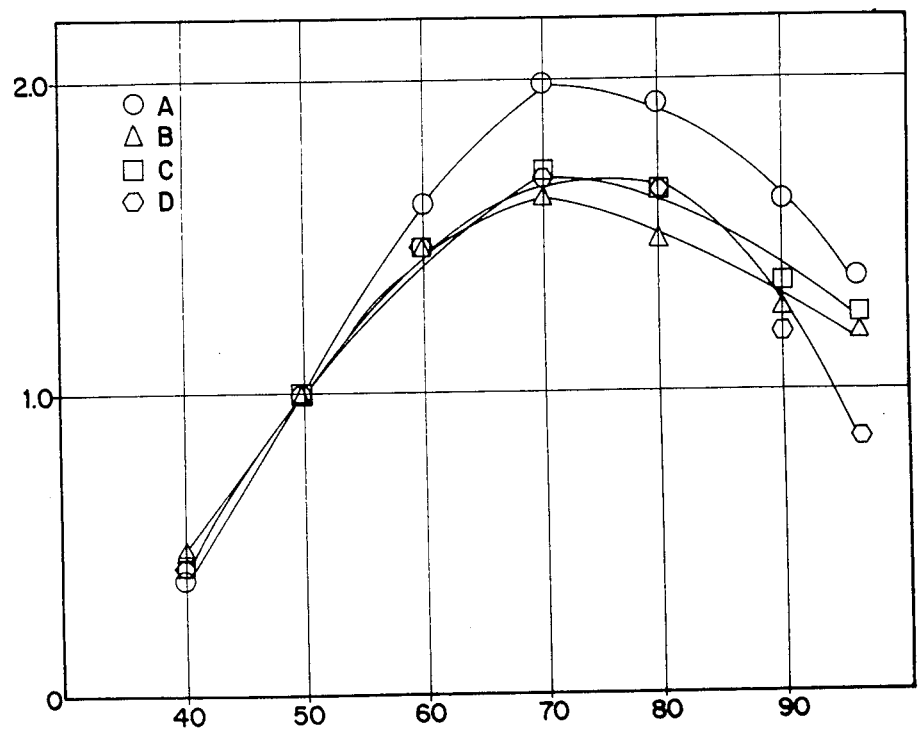

FIG. 2 illustrates the effect of the temperature on the activity of the described α-amylases. The abscissa reflects the temperatures in degrees centigrade and the ordinate reflects the relative activities at the corresponding temperature with respect to that obtained in the standard test at 50° C. Curves A, B, C and D correspond to the same enzymes as FIG. 1, as well as the buffers used and the calcium ion concentration. The α-amylases of the present invention, as that contained in *B. Stearothermophilus* ATCC 31199 described in U.S. Pat. No. 4,284,722 and Termamyl 120 of Novo, have under these conditions a maximum activity at 70°–80° C. However, from a practical point of view, we should admit at least two types of optimum conditions. Firstly, those affecting the maximum activity, and secondly those affecting the stability. Therefore, a distinction should be made between the optimum conditions for activity and those for stability which, on the other hand, need not coincide.

The molecular weight of the α-amylases of this invention has been determined by electrophoresis. Thus, disk and plate electrophoresis have been carried out on polyacrylamide gel in the presence of sodium dodecyl sulphate (SDS). The addition of SDS permits the proteins to be dissociated, wherefore the electrophoretic mobility thereof, in the corresponding gels, is a linear function of the logarithm of the molecular weights thereof. However, this method only permits the molecular weight of the denaturalized enzymes to be obtained. Therefore, another determination was carried out based on the migration of the proteins in acrylamide gels having different concentrations. The results of both methods are substantially in agreement. Hence, a molecular weight of 57,000 daltons for α-amylase of Bacillus sp. NCIB 11887, and 55,000 daltons for that of *Bacillus licheniformis* NCIB 11874 has been estimated. This value is definitely lower than that of α-amylase of *B. Stearothermophilus* ATCC 31199 cited in U.S. Pat. No. 4,284,722.

The stabilization of the α-amylases, in general, by $Ca^{++}$ has been known for many years. However, the negative aspect of the need of said cation as a stabilizer has previously been mentioned. In our case, we have observed that the α-amylases of the present invention are stable in the presence of low $Ca^{++}$ levels. Specifically, it has been observed that the half life of the α-amylase, in the absence of a substrate, at high temperatures (80° to 100° C.) is longer than that corresponding to NOVO's Termamyl 120 (T-120) and similar to that of the α-anylase produced by *B. Stearothermophilus* ATCC 31199 described in U.S. Pat. No. 4,284,722, for low $Ca^{++}$ concentrations. Table 3 illustrates some of the results obtained.

TABLE 3

| Type α-Amylase | T (°C.) | Half life (min.) ppm $Ca^{++}$ | | |
|---|---|---|---|---|
| | | 5 | 36 | 87 |
| T-120 | 80 | 5 | 34 | 120 |
| T-120 | 90 | 1 | 7 | 18 |
| Stearothermophilus ATCC 31199 | 80 | 14 | 49 | 98 |
| Stearothermophilus ATCC 31199 | 90 | 4 | 16 | 23 |
| Bacillus sp. NCIB 11887 | 80 | 13 | 44 | 92 |
| Bacillus sp. NCIB 11887 | 90 | 3 | 14 | 23 |

Incubation at pH 5.70 (Tris-maleate buffer)

Thus, it is clear that the α-amylases of the present invention are very suitable in processes for liquefying starch for the conversion thereof to dextrins. They are specially suitable for these processes due to the activity thereof at low pH's and high temperatures, as well as due to the high stability thereof even in the presence of very low $Ca^{++}$ levels.

This fact, as will be seen in the subsequent Examples, has been confirmed by hydrolysis carried out on corn starch (Example 8) and soluble potato starch (Example 7).

Upon hydrolyzing 30-35% (weight/volume) suspensions of soluble potato starch, at pH 5.7, 80° C., and without exogenous addition of $Ca^{++}$, with 4.5 cepsa α-amylase units from Bacillus sp. NCIB 11887 per gram of starch, a D.E. of 14-16% is obtained in 3 hours. These values are similar to those obtained with Novo's Termamyl 120 and the α-amylase of the *B. Stearothermophilus* ATCC 31199 described in U.S. Pat. No. 4,284,722 under the same conditions. Likewise, during the same time, the viscosity of the mentioned starch suspension is reduced from about 1,000 cps to less than 20 cps. These, and other facts, confirm that the amylases obtained by the present invention are true liquefying α-amylases. Furthermore, when hydrolyzing 30-50% (weight/volume) corn starch suspensions with α-amylases of Bacillus sp. NCIB 11887, at pH 5.3 and 185 ppm $Ca^{++}$, a D.E. of from 14-16% is reached in 3 hours. In these cases, hydrolysis is carried out maintaining the reaction mixture for 5-10 minutes at 105°-110° C. and for 3 hours at 95° C. using 4.0 cepsa α-amylase units/gr of starch.

The following Examples illustrative of the invention are not limiting thereof. Obviously changes and modifications known to the experts in the art can be introduced therein.

EXAMPLE 1

Four 250 ml erlenmeyer flasks were filled with 100 ml of culture broth having the compositions indicated in the Table. The four flasks were inoculated with a strain of *Bacillus licheniformis* ATCC 8480. After 7 to 9 days' culture at 30° C. in an incubator stirred at 210 r.p.m., the mentioned activities were obtained in the culture broth.

| Culture broth | AM-33 | AM-33 bis | AM-37 | AM-69 |
|---|---|---|---|---|
| Soluble starch (g/l) | 40 | 40 | 30 | 30 |
| Ground Barley (g/l) | 100 | — | — | — |
| Barley extract (g/l) | — | 100 | — | — |
| Soybean meal (g/l) | 30 | — | — | — |
| Peptone (g/l) | — | — | 5 | 5 |
| $Na_2SO_4$ | 1 | 1 | — | — |
| $CaCO_3$ (g/l) | 4 | 4 | — | — |
| $CaCl_2$ (g/l) | — | — | 0.4 | 1 |
| $MnSO_4$ (g/l) | — | — | 0.5 | 0.5 |
| $MgCl_2$ (g/l) | — | — | 0.5 | 1.5 |
| KCl (g/l) | — | — | 0.5 | 0.5 |
| Trizma base (g/l) | — | — | — | 6 |
| Tween 80 (ml/l) | 0.1 | 0.1 | — | — |
| pH = 7.5 | | | | |

| Culture broth | Broth activity (CEPSA u/ml.) |
|---|---|
| AM 33 | 34 |
| AM 33 bis | 14 |
| AM 37 | 3 |
| AM 69 | 0 |

The need to use very concentrated media containing ground barley or barley extract to achieve significative activities in the broth when the micro-organism is cultured at 30° C., can clearly be seen.

Two 2L fermentors were then prepared, one with 1,125 cc of AM-33 bis culture broth and the other with 1,125 cc of AM-69 culture broth containing the previously mentioned composition, to which there were added antifoam agents to prevent the formation of foam; they were sterilized and incoulated with a strain of *Bacillus licheniformis* ATCC 8480. The proportion of the inoculum was of 10%.

Growth took place at a temperature of 30° C. with an aeration of 1.3 v/v/min. and a stirring speed of 1,750 r.p.m.

The tests were repeated under similar conditions with the exception of the culturing temperature which was raised to 56° C. and the inoculum used, which was a strain of *Bacillus licheniformis* ATCC 8480, adapted to grow at high temperatures. The proportion of inoculum used was also of 10%.

The inoculum for the fermentor containing AM-69 culture medium was prepared as follows: The strain of *Bacillus licheniformis* ATCC 8480 was re-seeded in an inclined AM-8 agar tube, it was cultured at 56° C. for 48 hours. The culture grown in AM-8 was washed with a solution of 9% NaCl and the thusly obtained suspension served as the inoculum for a 250 ml erlenmeyer flask containing 100 ml of the previously mentioned AM-33. Incubation took place for 14 days at 56° C. and 210 r.p.m. 14 days thereafter, 10 ml of this culture served as the inoculum for a 250 ml erlenmeyer flask containing 100 ml of the AM-76 culture medium. It was incubated at 56° C. for 72 hours at 210 r.p.m. This culture served as the inoculum for the fermentor.

The composition of the AM-76 culture medium was the following:

| | |
|---|---|
| Soluble starch (g/l) | 5 |
| Peptone (g/l) | 5 |
| CaCl$_2$ (g/l) | 1 |
| Mn SO$_4$ (g/l) | 0.5 |
| Mg Cl$_2$ (g/l) | 1.5 |
| K Cl (g/l) | 0.5 |
| Trizma base (g/l) | 6 |
| pH = 7.5 | |

The inoculum for the fermentor containing AM-33 culture medium was prepared following the first two steps of the preceding case. After 14 days' growth 10 ml of culture served as the inoculum for a 250 ml erlenmeyer flask containing 100 ml of AM-33 culture medium, it was incubated for 72 hours at 210 r.p.m. at 56° C. and this culture served as the inoculum for the fermentor.

| AM-8 culture medium | |
|---|---|
| Starch (g/l) | 40 |
| Peptone (g/l) | 10 |
| Agar-agar (g/l) | 20 |

Growth took place at 56° C. with an aeration of 1,3 v/v/min. and a stirring speed of 1,750 r.p.m.

The results obtained in the two tests are as follows:

| | Temperature °C. | | | |
|---|---|---|---|---|
| | 30 | | 56 | |
| Culture medium | Activity u/CEPSA/ml. | Time of culture (h) | Activity u/CEPSA/ml. | Time of culture (h) |
| AM 33 bis | 14 | 164 | 45 | 113 |
| AM 69 | 6 | 101 | 225 | 89 |

It is clearly demonstrated that at a high temperature, contrary to what takes place at 30° C., the poor medium not containing barley is the most adequate for the production of α-amylase, furthermore obtaining a substantial saving in the culturing time. Thus, the adaptation to high temperatures not only increases the speed of growth, but also produces a substantial alteration of the metabolic pattern of the micro-organism.

EXAMPLE 2

Three 250 ml erlenmeyer flasks were filled with 100 ml of AM-76 culture broth described in Example 1. The three flasks were inoculated with a strain of Bacillus licheniformis ATCC 27811 and incubated at temperatures of 30°, 45° and 56° C. at 210 r.p.m. After 3-4 days' culture, the following results were obtained:

| Temperature (°C.) | Activity broth (CEPSA u/ml) | Time of Culture (h) |
|---|---|---|
| 30 | 4 | 72 |
| 45 | 4 | 96 |
| 56 | 112 | 72 |
| 56 | 172 | 96 |

As in the case of the strain of Bacillus licheniformis ATCC 8480, the production of α-amylase increased as the culturing temperature of the micro-organism increased.

EXAMPLE 3

A 2 L fermentor was filled with 1,125 cc of the AM-69 culture medium described in Example 1, to which there was added an antifoam agent to prevent the formation of foam, it was sterilized and inoculated with a culture of the strain of Bacillus licheniformis NCIB 11874, capable of growing at high temperatures. The inoculum was prepared following the procedure described in Example 1. The culture was carried out at a temperature of 60° C., aeration of 1,3 v/v/min and a pH of 7.5 with a stirring speed of 1,750 r.p.m. Under these conditions and 40 hours thereafter, an activity in the culture broth of 270 cepsa units/ml. was reached.

EXAMPLE 4

A 2 L fermentor was filled with 1,125 cc of AM-96 culture medium to which an antifoam agent was added to prevent the formation of foam, it was sterilized and inoculated with a culture of the strain of Bacillus licheniformis NCIB 11874, capable of growing at high temperatures. The inoculum was prepared as described in Example 1, with the exception that the AM-79 instead of the AM-76 culture medium was used.

The culture was carried out at a temperature of 60° C., aeration of 1,3 v/v/min, and a pH of 7.5 with a stirring speed of 1,750 r.p.m. Under these conditions and 63 hours thereafter, an activity in the culture broth of 317 cepsa unit/ml. was reached.

Composition of the culture broths:

| | AM-79 | AM-96 |
|---|---|---|
| Soluble starch (g/l) | 5 | 30 |
| Yeast extract (g/l) | 5.07 | 5.07 |
| Ca Cl$_2$ (g/l) | 1 | 1 |
| Mn SO$_4$ (g/l) | 0.5 | 0.5 |
| Mg Cl$_2$ (g/l) | 1.5 | 1.5 |
| K Cl (g/l) | 0.5 | 0.5 |
| Trizma base (g/l) | 6 | 6 |
| pH = 7.5 | | |

EXAMPLE 5

Four fermentors containing AM-69 culture medium (described in Example 1) were inoculated with the following strains: Bacillus stearothermophilus ATCC 31199, Bacillus licheniformis NCIB 11874, Bacillus sp. NCIB 11887 and Bacillus circulans ATCC 21822. The culturing conditions used, in all cases, were the following: 56° C. temperature, pH 7.5, aeration 1,3 v/v/min. and a stirring speed of 1,750 r-p.m. After 60-80 hours' culturing same was stopped, the broth was centrifuged to remove the cellular debris and the heat stability of the α-amylases produced was tested.

The process used to determine the heat stability of these α-amylases will now be described. The culture broth was diluted in a Tris-maleate buffer, pH 5.70, so that the final concentration of the enzyme was of about 4 cepsa units/ml. of solution. At the same time, the concentration of Ca$^{++}$ ions was adjusted to 5.25 or 36 ppm, depending on the test. The estimation of the residual activity in each case, after incubation for 15 minutes at 80° C., permitted the following values to be obtained:

| | Residual activity (%) | | |
|---|---|---|---|
| Ca++ (ppm) | 5 | 25 | 36 |
| Enzyme origin: | | | |
| B. Stearothermophilus ATCC 31199 | 43 | — | 71 |
| B. licheniformis NCIB 11874 | 27 | — | 75 |
| Bacillus sp NCIB 11887 | 34 | 56 | 77 |
| B. circulans ATCC 21822 | 45 | 54 | — |

Whereas, under these conditions, Novo's Termamyl 120 retained 80% of its initial activity in the presence of 36 ppm Ca++, but it was completely deactivated, even after 10 minutes' incubation, if only 5 ppm Ca++ were added.

If the same test is repeated, but incubating the α-amylases at 90° C., the results obtained 15 minutes thereafter are the following:

| | Residual Activity (%) | |
|---|---|---|
| Ca++ (ppm) | 25 | 36 |
| Enzyme origin: | | |
| B. Stearothermophilus ATCC 31199 | — | 50 |
| B. licheniformis NCIB 11874 | — | 54 |
| Bacillus sp. NCIB 11887 | 17 | 46 |
| B. circulans ATCC 21822 | 19 | — |

Whereas, under these same conditions, Novo's Termamyl 120 retains 17% of its initial activity in the presence of 35 ppm Ca++.

EXAMPLE 6

A 2 L fermentor was filled with 1,125 cc of the AM-69 culture medium, it was sterilized an inoculated with a culture of the strain *Bacillus circulans* ATCC 21822. The proportion of the inoculum was of 10%. The culturing conditions for the inoculum grown in AM-76 were of from 20 to 24 hours at 56° C. and at 210 r.p.m. The culture in the fermentor was carried out at a temperature of 56° C., aeration of 1,3 v/v/min. and a pH of 7.5 with a stirring speed of 1,750 r.p.m. Before sterilizing the medium, an antifoam agent was added to prevent the formation of foam. Under these conditions and 48 hours thereafter, an activity in the culture medium of 200 cepsa units/ml. was reached.

EXAMPLE 7

The culture broths from different α-amylase producers, obtained as described in Example 3 were used to hydrolyze a soluble 33% potato starch solution (weight/volume) in a Tris-maleate buffer, pH 5.70. Thus, a starch suspension was prepared in the least possible amount of the mentioned buffer. Said suspension was poured onto a boiling buffer, boiling and stirring were maintained until the complete solubilization of the starch. Then 1.5 cepsa α-amylase units/ml. of starch solution were added, equivalent to 4.55 cepsa α-amylase units/g of starch. Hydrolysis of the starch was immediately initiated at 80° C.

This hydrolysis process is conducted with crude or partially purified enzymes. In the first case, the α-amylases contained in the culture broth were directly used, while in the second case the α-amylases used originated from a purification process with organic solvents. Therefore, the α-amylases present in the broths were precipitated with 60% (volume/volume) of acetone, at 0° C. and under stirring. The thusly obtained precipitates were re-suspended in Tris-HCl buffer, pH 7.0.

The hydrolytic process was controlled with D.E. (dextrose equivalent) analysis and distribution of oligomers in the different samples. The D.E. was determined according to the Lane-Eynon method, while the different degrees of polymerization of the oligomers resulting from the hydrolysis was calculated by high pressure liquid-liquid chromatography. Tables 5 and 6 summarize the values obtained for the different types of α-amylases.

As can be observed in Table 5 there are no substantial differences, with respect to the evolution of the D.E. (%) in the hydrolysates, between the different types of α-amylases tested. Likewise, substantial differences are not detected as a result of the use of crude or partially purified enzyme.

TABLE 5

| Type of α-amylase | Hydrolysis time (min.) | | | | |
|---|---|---|---|---|---|
| | 30 | 60 | 90 | 120 | 180 |
| B. stearoterm. ATCC 31179 | | | | | |
| (a) Crude | 6.7 | 8.7 | 8.7 | 11.1 | 14.5 |
| (b) Purified | 4.3 | 6.5 | 9.0 | 11.3 | 15.2 |
| B. licheniformis NCIB 11874 | | | | | |
| (a) Crude | 3.9 | 7.5 | 8.7 | 8.7 | 15.5 |
| (b) Purified | 6.4 | 8.2 | 10.5 | 13.4 | 15.4 |
| Bacillus sp. NCIB 11887 | | | | | |
| (a) Crude | 6.4 | 8.9 | 10.5 | 13.2 | 15.4 |
| (b) purified | 7.0 | 11.1 | 13.0 | 15.5 | 16.8 |
| B. circulans ATCC 21822 | | | | | |
| (a) Crude | 3.3 | 7.6 | 9.3 | 11.2 | 12.6 |
| (b) Purified | 4.0 | 8.1 | 9.5 | 12.2 | 14.0 |
| T-120 Novo | 6.2 | 9.0 | 11.4 | 13.1 | 15.1 |
| Bacillus sp. NCIB 11886 | | | | | |
| (a) Purified | 7.0 | 11.8 | 12.9 | 16.1 | 16.8 |

On the other hand, Table 6 illustrates that the distribution of oligomers in the hydrolysates differ according to the type of α-amylase used. In general, the α-amylases produced by *Bacillus licheniformis*, such as NCIB 11874 and Novo T-120 yield a higher proportion of oligomers having a low molecular weight than the remaining enzymes.

Nevertheless, the slight differences appearing in the distributions of oligomers of the different enzymes, do not noticeably affect the yields of the industrial application thereof.

TABLE 6

| Type of α-amylase | Hydrolysis Time (min.) | $DP_1$ (%) | $DP_2$ (%) | $DP_3$ (%) | $DP_4$ (%) | $DP_5$ (%) | $DP_6$ (%) | $DP_7$ (%) | $DP_{8+}$ (%) |
|---|---|---|---|---|---|---|---|---|---|
| T-120 | 60 | 1.4 | 4.6 | 7.6 | 5.9 | 5.6 | 10.8 | 4.8 | 59.3 |
| NOVO | 120 | 2.0 | 8.8 | 13.1 | 8.3 | 9.1 | 13.9 | 14.2 | 30.6 |
| B. stearoterm. ATCC-3199 | 60 | 1.2 | 4.1 | 7.2 | 3.9 | 3.4 | 13.0 | 4.6 | 52.6 |
| | 120 | 2.6 | 6.9 | 9.6 | 4.1 | 4.6 | 20.5 | 0.2 | 51.5 |
| B. lichenif. | 60 | 0.6 | 3.3 | 9.9 | 4.9 | 10.5 | 9.4 | 0.6 | 60.8 |

TABLE 6-continued

| Type of α-amylase | Hydrolysis Time (min.) | DP$_1$ (%) | DP$_2$ (%) | DP$_3$ (%) | DP$_4$ (%) | DP$_5$ (%) | DP$_6$ (%) | DP$_7$ (%) | DP$_{8+}$ (%) |
|---|---|---|---|---|---|---|---|---|---|
| NCIB 11874 | 120 | 0.8 | 5.2 | 12.2 | 6.1 | 15.1 | 10.3 | 0.3 | 50.0 |
| Bacillus sp. | 60 | Trazas | 1.7 | 6.3 | 1.3 | 3.5 | 12.1 | 9.9 | 65.2 |
| NCIB 11887 | 120 | Trazas | 4.6 | 8.3 | 1.6 | 9.1 | 17.1 | 8.2 | 51.1 |
| B. circulans | 60 | Trazas | 2.3 | 6.0 | 2.8 | 3.1 | 10.7 | 9.5 | 65.6 |
| ATCC 21822 | 120 | Trazas | 3.9 | 7.2 | 1.5 | 3.7 | 13.8 | 7.3 | 62.6 |

EXAMPLE 8

Various α-amylases producing strains were cultured as described in Example 5. Then the corresponding enzymes were purified and recovered according to the procedure described in Example 7. The resulting α-amylases were tested in the hydrolysis of corn starch, under conditions similar to those used industrially. Thus, different aqueous starch solutions were prepared, varying the $Ca^{++}$ concentration (by adding for example Ca Cl$_2$), the pH (adjusted with NaOH) and the concentration of the starch. In all these cases 4 cepsa α-amylase units/g of hydrolyzed starch were used. The evolution of the temperature during the process took place as follows: immediately after adding the enzyme, the suspension was rapidly heated to 105°–110° C., this temperature was then maintained for 5 minutes and finally the suspension was cooled to 95° C., at which temperature the mixture was maintained for 3 hours.

In the event suspensions containing 43.5% (weight/volume) of starch were hydrolyzed in the presence of 185 ppm $Ca^{++}$, the final D.E. (%) for each case were the following:

| Type of α-amylase | Final D.E. (%) | pH hydrolysis |
|---|---|---|
| B. stearothermophilus ATCC 31199 | 13.3 | 5.7 |
| B. licheniformis NCIB 11874 | 14.6 | 5.7 |
| Bacillus sp NCIB 11887 | 16.5 | 5.7 |
| T-120 Novo | 18.7 | 6.2 | with 40% starch suspensions and a hydrolysis pH of about 5.4, the final D.E. (%) for different $Ca^{++}$ concentrations were the following:

| Type of α-amylase | Final D.E. (%) 185 ppm $Ca^{++}$ | Final D.E. (%) 35 ppm $Ca^{++}$ |
|---|---|---|
| B. stearothermophilus ATCC 31199 | 17.3 | 12.2 |
| B. licheniformis NCIB 11874 | 18.9 | 8.7 |
| Bacillus sp. NCIB 11887 | 17.7 | 12.2 |
| B. circulans ATCC 21822 | — | 12.8 |
| T-120 Novo | 20.3 | 11.3 |

Finally, when the suspension containing 35% (weight/volume) of starch was hydrolyzed, in the presence of 185 ppm $Ca^{++}$, at a pH of 5.3, the following results were obtained:

| Type of α-amylase | Final D.E. (%) |
|---|---|
| B. stearothermophilus ATCC 31199 | 8.5 |
| B. licheniformis NCIB 11874 | 14.5 |
| Bacillus sp. NCIB 11887 | 15.5 |
| B. circulans ATCC 21822 | 12.5 |
| T-120 Novo | 7.1 |

EXAMPLE 9

A 2 L fermentor was filled with 1,125 cc of the AM-69 culture broth, to which an antifoam agent was added to prevent the formation of foam. The thusly prepared fermentor was sterilized and inoculated with the AM-76 culture medium described in Example 1 of the strain Bacillus sp. NCIB 11887. The culturing conditions for the inoculum were of 20 hours at 56° C. and 210 r.p.m. The culture in the fermentor was carried out at a temperature of 60° C., aeration of 1.3 v/v/min., pH 7.5, and a stirring speed of 1,750 r.p.m. Under these conditions an activity of 380 cepsa units/ml. were obtained 53 hours after culturing.

EXAMPLE 10

The strain of Bacillus sp. NCIB 11887 was treated with NG to obtain mutants. From the 350 colonies obtained, after measuring the α-amylase activity, the strain 3666 (registered in the NCIB under No. 11886) was selected.

Strain 3666 was cultivated in two 2 L fermentors: one containing 1,125 cc of the AM-69 culture medium and the other containing 1,125 cc of the AM-96 culture medium described in Example 4. An antifoam agent was added to the two fermentors to prevent the formation of foam. One of the thusly prepared fermentors was inoculated with a culture of the strain 3666 grown in AM-76 described in Example 1 and the other with a culture of strain 3666 grown in AM-79 described in Example 4, respectively. The culturing conditions of the inoculums were: 20 hours at 56° C. and 210 r.p.m.

Culturing in fermentors took place at a temperature of 60° C., aeration of 1.3 v/v/min, and a stirring speed of 1,750 r.p.m. Under these conditions the following results were obtained:

| Culture Medium | Activity broth (cepsa u/ml.) | Culturing time (hr) |
|---|---|---|
| AM-69 | 370 | 89 |
| AM-96 | 400 | 44 |

EXAMPLE 11

Six 2 L fermentors were filled with 1,125 cc of the AM-96 culture medium to which an antifoam agent was added to prevent the formation of foam. They were sterilized and inoculated with a culture of strain 3666 grown in AM-76 described in Example 4. The culturing conditions for the inoculum were of 20 hours at 56° C. and 210 r.p.m. Culturing in the fermentor was carried out under the following conditions: Aeration 1.3 v/v/min., stirring speed 1,750 r.p.m. In three of the fermentors the influence of the temperature was studied and the pH was of 7.5, the temperatures to be studied being of 55°, 60°, 65° C. In the three remaining fermentors, the influence of the pH was studied, the culturing temperature being of 60° C. and the pH to be studied of 6.5, 7.5 and 8. Under these conditions the following results were obtained:

| Temp. °C. | pH | Batch | | Fed Batch | |
|---|---|---|---|---|---|
| | | Culturing Time (h) | Activity Cepsa u/ml. | Culturing Time (h) | Activity Cepsa u/ml. |
| 55 | 7.5 | 68 | 290 | 57 | 197 |
| 60 | 7.5 | 68 | 385 | 63 | 224 |
| 65 | 7.5 | 68 | 52 | 69 | 154 |
| 60 | 6.5 | 40 | 156 | 34 | 325 |
| 60 | 7.5 | 40 | 215 | 34 | 423 |
| 60 | 8 | 40 | 147 | 40 | 85 |

EXAMPLE 12

Two cultures of the micro-organism *B. licheniformis* NCIB 11874, Bacillus sp. NCIB 11887 were prepared in 250 ml erlenmeyer flasks containing 100 ml of the AM-79 culture medium (See Example 4). The cultures were incubated at 56° C. for 72 hours in an orbital stirrer (210 r.p.m.). At the end of the culture, the enzymes were recovered following the procedure described in Example 7. The partially purified enzymes, using acetone, were subsequently purified by precipitation of the corresponding enzyme-starch complexes, as described by Michael Schram and Abraham Loyter in "Methods in Enzymology" Vol. VIII, pages 533–537. The purified enzymes were subjected to electrophoresis in polyacrylamide gels with sodium dodecyl sulphate to determine the molecular weight thereof. For this purpose the technique described by K. Weber and M. Osborn in J. Biol. Chem. 244, 4406 (1969) was used, and albumina (P.M. 67000), catalase (P.M. 60000) ovalbumina (P.M. 43000) and LDH (P.M. 36000) were used. This technique permits a molecular weight of 55,000 daltons for the α-amylase of *B. licheniformis* NCIB 11874 and of 57,000 daltons for Bacillus sp. NCIB 11887, to be determined.

We claim:

1. A process for producing thermostable α-amylases by culturing micro-organisms at elevated temperatures comprising the aerobic submerged culturing of a strain selected from the micro-organisms Bacillus sp. NCIB 11887 or NCIB 11886, or any of the mutants thereof, in a suitable culture medium and recovering the thusly produced enzyme from the culture broth.

2. A process for producing thermostable α-amylases by culturing micro-organisms at elevated temperatures according to claim 1, wherein the culturing temperature is of from 50° to 70° C.

3. A process for producing thermostable α-amylases by culturing micro-organisms at elevated temperatures according to claims 1 or 2, comprising the culture of a strain of Bacillus sp. selected from NCIB 11887, NCIB 11886 or any of the mutants thereof, and characterized in that the culture medium used contains a source of carbon, a source of organic nitrogen, and suitable trace substances.

4. A process for producing thermostable α-amylases by culturing micro-organisms at elevated temperatures according to claim 3, wherein the culturing temperature is from 50° to 70° C., and a pH of from 5 to 8.

5. A thermostable α-amylase obtained by a process according to claim 3, characterized by the following characteristics:
   a molecular weight, measured by electrophoresis in a polyacrylamide gel, of 57,000 daltons;
   suspended in a tris-maleate buffer, pH 5.7, and at 80° C., it has a half-life with respect to its activity of about 44 in the presence of 36 ppm calcium ion, and of about 92 minutes in the presence of 87 ppm calcium ion;
   a maximum activity temperature at pH 5.7 and with 10 to 20 ppm calcium of about 80° C.

6. A process for producing thermostable α-amylase by culturing micro-organisms at elevated temperature according to claim 2 wherein the culturing temperature is from 55° to 65° C.

7. A process for producing thermostable α-amylases by culturing micro-organisms at elevated temperatures according to claim 3, wherein the source of carbon is selected from starch or its hydrolysates having a concentration of from 5 to 60 g/l, the source of organic nitrogen being selected from the group consisting of peptone, yeast extract and corn steep liquor.

8. A process for producing thermostable α-amylase by culturing micro-organisms at elevated temperatures according to claim 4, wherein the culturing temperature is from 55° to 65° C. and the pH is from 7 to 7.5.

* * * * *